United States Patent [19]
Sato et al.

[11] Patent Number: 5,959,148
[45] Date of Patent: Sep. 28, 1999

[54] PURIFICATION PROCESS OF N-VINYLFORMAMIDE

[75] Inventors: Shin-ichi Sato; Takahiro Oshida; Hiroshi Izumikawa; Akihiko Tanaka; Eiichiro Koresawa, all of Kitakyusyu, Japan

[73] Assignee: Mitsubishi Chemical Corporation, Tokyo, Japan

[21] Appl. No.: 08/828,472

[22] Filed: Mar. 31, 1997

[51] Int. Cl.$^6$ .................. C07C 231/24; C07C 233/03
[52] U.S. Cl. ............................. 564/206; 564/204
[58] Field of Search ..................... 564/204, 206

[56] References Cited

U.S. PATENT DOCUMENTS

| | | | |
|---|---|---|---|
| 4,578,515 | 3/1986 | Dawson et al. | 564/215 |
| 4,814,505 | 3/1989 | Kroener et al. | 564/216 |
| 5,554,792 | 9/1996 | Sawayama et al. | 564/4 |

FOREIGN PATENT DOCUMENTS

| | | | |
|---|---|---|---|
| 3132868 | 6/1988 | Japan | 564/206 |
| 3190862 | 8/1988 | Japan | 564/206 |
| 5-155829 | 6/1993 | Japan . | |
| 6-122660 | 5/1994 | Japan . | |
| 6-99374 | 12/1994 | Japan . | |
| 8-48657 | 2/1996 | Japan . | |

*Primary Examiner*—Shailendra Kumar
*Attorney, Agent, or Firm*—Dike, Bronstein, Roberts & Cushman, LLP; David G. Conlin; George W. Neuner

[57] ABSTRACT

A purification process of N-vinylformamide, which comprises: providing a crude N-vinylformamide having an acetone-insoluble component content of not more than 400 ppm; and continuously feeding the crude N-vinylformamide into a fractionating tower, to obtain an N-vinylformamide having high purity. Also disclose is a continuous purification process of N-vinylformamide, which comprises the steps of: providing a crude N-vinylformamide; feeding the crude N-vinylformamide into a thin film evaporator to remove un-evaporated fraction from the system, and feeding the evaporated fraction containing N-vinylformamide into a fractionating tower, distilling the purified N-vinylformamide from the tower head, and discharging a bottom liquid containing N-vinylformamide from the tower bottom, and recycling the bottom liquid into the thin film evaporator to remove un-evaporated fraction from the system, and feeding the evaporated fraction into the fractionating tower.

19 Claims, 2 Drawing Sheets

PURIFICATION PROCESS OF N-VINYLFORMAMIDE

FIELD OF THE INVENTION

The present invention relates to a distillation purification process of N-vinylformamide. More specifically, it relates to a process for the purification of N-vinylformamide to high purity, in which a distillation apparatus is prevented from choking caused by thermally polymerized products of N-vinylformamide.

BACKGROUND OF THE INVENTION

It is known that N-vinylformamide is a compound having high polymerizability and useful as a material of polyvinylamine and other water soluble polymers and as an intermediate of organic chemicals. However, N-vinylformamide having a higher purity has been demanded. Typical known production methods of N-vinylformamide include a method in which an alcohol is eliminated from N-($\alpha$-alkoxyethyl) formamide as described in U.S. Pat. No. 3,914,304, a method in which hydrogen cyanide is eliminated from formylalaninenitrile as described in JP-A-61-134359 (the term "JP-A" as used herein means an "unexamined published Japanese patent application") and a method in which ethylidenebisformamide is decomposed with heat as described in U.S. Pat. No. 4,490,557 and U.S. Pat. No. 4,578,515. In all of these methods, N-vinylformamide is obtained by thermal decomposition at a high temperature of 100° C. or more under a reduced pressure. From the thermal decomposition reaction solution, a crude N-vinylformamide generally having a purity of 80% by weight or more can be recovered by distillation removal of low boiling point ingredients and the like. The crude N-vinylformamide generally contains eliminated molecules of the precursor, such as alcohols and formamide. In many cases, it also contains various acidic and basic substances by-produced at the time of the thermal decomposition. These impurities exert adverse influences such as reduction of the yield in the subsequent purification step and decrease in the molecular weight in the polymerization or reaction step, to thereby considerably spoil the quality of a final product.

In order to obtain high purity N-vinylformamide by purifying a crude N-vinylformamide, a method in which a crude N-vinylformamide is continuously distilled using a fractionating tower is considered to be most effective. However, since N-vinylformamide has extremely high reactivity, there is a danger of causing a thermal decomposition reaction, a thermal polymerization reaction and the like, which are undesirable side reactions during the distillation. Particularly, the thermal polymerization reaction frequently causes formation of insoluble and infusible polymer compounds, and this results in the choking of a distillation apparatus. As a result, the distillation recovery yield is extremely reduced and a continuous use of the distillation becomes difficult. Such problems occur even under relatively moderate operation conditions of industrial scale continuous distillation, namely under a reduced pressure of generally from 0.1 to 3 KPa as a distillation tower head pressure, which corresponds to the tower head temperature of about 50 to 100° C. as.

Several methods have been proposed as a method for stably effecting distillation of N-vinylformamide, such as a method in which a crude N-vinylformamide is distilled with previously adjusting its pH value, as described in JP-A-62-195352, JP-A-6-122661, and a method in which distillation of a crude N-vinylformamide is carried out with previously adding a specific stabilizing agent, as described in JP-A-61-289068, JP-A-8-48657, etc. Also, JP-A-62-190153 proposes a method in which a crude N-vinylformamide containing 1 to 70% of formamide is subjected to distillation.

However, most of the conventional methods for stably distilling N-vinylformamide are based on the knowledge obtained in laboratory level, i.e., small scale batch distillation tests, so that prevention of thermal polymerization in a long-term continuous distillation is still insufficient, sometimes causing formation of insoluble and infusible polymers. Further, though examples of continuous distillation are known, as described in U.S. Pat. 4,814,505 (corresponding to JP-A-62-190153) and JP-A-5-155829, they have a problem, for example, in that a crude N-vinylformamide contains a large-amount of formamide or that purity of the N-vinylformamide recovered by continuous distillation is still insufficient.

Particularly, whereas a crude N-vinylformamide generally contains a small amount of formamide formed during synthetic steps, the continuous distillation in the case of the example disclosed in the specification of U.S. Pat. No. 4,814,505 is carried out using a crude N-vinylformamide containing about 35% of formamide prepared by adding a large amount of formamide. Such a method may be effective in preventing thermal polymerization, but it is necessary to employ an additional step for the recovery and purification of formamide used in excess amount. Therefore, this method cannot be advantageous for industrial application.

SUMMARY OF THE INVENTION

In view of the above, it is therefore an object of the present invention to provide an industrially advantageous method for the purification of N-vinylformamide by distillation, particularly by continuous distillation using a fractionating tower, in which polymerization in the tower is prevented and by which N-vinylformamide having high purity is produced with high yield.

Other objects and advantages of the present invention will become more apparent from the following description.

The inventors of the present invention have conducted extensive studies to solve the above described problems in conventional techniques and to achieve the above objects of the present invention. As a result, the inventors found that when a crude N-vinylformamide is purified using a fractionating tower, minor components which is generally contained in the crude N-vinylformamide and regarded as to have relatively high molecular weights are the main cause for the thermal polymerization during distillation. The present invention has been accomplished based on this finding.

Accordingly, the present invention relates to a process for the purification of a crude N-vinylformamide, which comprises:

providing a crude N-vinylformamide having an acetone-insoluble component content of not more than 400 ppm; and continuously feeding the resulting material into a fractionating tower to effect distillation, to thereby obtain an N-vinylformamide having high purity.

DETAILED DESCRIPTION OF THE INVENTION

The production process of the crude N-vinylformamide for use in the purification process of the present invention is not particularly limited, and the methods exemplified above may be used. However, the method in which an alcohol is eliminated from N-(α-alkoxyethyl)formamide is preferred as a thermal decomposition method because of the high N-vinylformamide yield and no by-production of toxic substances such as hydrogen cyanide and the like.

Since the reaction solution containing N-vinylformamide is a mixture which contains not only N-vinylformamide but also alcohols and formamide as by-products, low boiling point alcohols such as methanol, ethanol and the like can be efficiently removed from the thermal decomposition reaction solution by evaporation under reduced pressure. In consequence, the thermal decomposition reaction solution may be subjected to the purification of the present invention directly as crude N-vinylformamide, but it is preferred in general to remove these low boiling point components in advance. The method for the evaporation treatment of low boiling point components may be a method in which low boiling point components in the mixture are evaporated under reduced pressure. For example, when a reaction solution containing N-vinylformamide obtained by the thermal decomposition method in which alcohols are eliminated from N-(α-alkoxyethyl)formamide is treated by this method, a crude N-vinylformamide having a purity of generally 70% or more, preferably 80 to 95% by weight, and having a formamide content of approximately from 1 to 10% by weight can be relatively easily obtained.

In this connection, the "crude N-vinylformamide" for use in the purification of the present invention means N-vinylformamide having a lower purity than that after the purification of the present invention, so that it includes not only the above described reaction solution from which low boiling point components or high boiling point components are removed to a certain degree, but also an N-vinylformamide once purified but having reduced purity due to deterioration after a long period of storage.

Next, the term "acetone-insoluble components in a crude N-vinylformamide" as used herein means substances which are formed as precipitates when 5 times weight of acetone is added at room temperature (25° C.) to a crude N-vinylformamide from which low boiling point components and the like are removed. These substances are identified as high boiling point components mainly comprising polymers of N-vinylformamide by an analysis of, for example, an IR spectrum, an NMR spectrum, a liquid chromatography and the like. These polymers are by-produced during a step of the production of the crude N-vinylformamide, such as a thermal decomposition step of a precursor such as N-(a-alkoxyethyl)formamide or the like. They are also formed and increase spontaneously during transportation and storage of a purified N-vinylformamide because of the high reactivity of N-vinylformamide itself. These acetone-insoluble components are dissolved in a crude N-vinylformamide under usual conditions.

The present inventors have found that, when such acetone-insoluble components are contained in the starting material, polymerization is accelerated using these component as nucleus, and growth of the polymer cannot be avoided even in the presence of a stabilizing agent. In a distillation tower, precipitation of insoluble substances is apt to occur where the packed material is not uniformly wetted. It is assumed that, once insoluble substances are precipitated, a polymer grows using these substances as nucleus, finally resulting in the accumulation of an insoluble and infusible polymer. Such a phenomenon is particularly significant at the material supplying inlet where these acetone-insoluble components are continuously supplied. In consequence, according to the present invention, it is necessary to remove acetone-insoluble components from the crude N-vinylformamide as much as possible prior to the continuous distillation purification, thereby reducing the content of high molecular weight components in the crude N-vinylformamide to 400 ppm or less, preferably 200 ppm or less, more preferably 50 ppm or less.

However, the situation becomes different when a crude N-vinylformamide having high formamide content is used as the raw material. Since formamide has high solubility even for such acetone-insoluble components, insoluble substances are not apt to precipitate but easily carried away into the tower bottom, so that such a problem is hardly realized. The influence of acetone-insoluble components is particularly significant when the formamide content of the crude N-vinylformamide is 10% or less. The crude N-vinylformamide usually contains formamide as its material, but it is preferred to reduce the formamide content as low as possible, preferably to 5% or less, from the viewpoint of material unit requirement. In case that such a crude N-vinylformamide is used, thermal polymerization in a fractionating tower is apt to quite frequently occur when it contains acetone-insoluble components.

Though not particularly limited, the following method may be used as a means to remove the above described acetone-insoluble components from the crude N-vinylformamide. For example, since acetone-insoluble components generally have high molecular weights and no vapor pressure, it is possible to separate them easily from N-vinylformamide by evaporation. In that case, the apparatus for use in the evaporation should be of such a type that it does not cause a problem such as choking and the like with respect to polymers previously contained in the material or formed during a unit operation, and therefore a thin film evaporator is particularly preferred for this purpose.

Such a thin film evaporator is suitable for use in the evaporation separation of a substance, e.g., N-vinylformamide, having not so high heat stability from a mixture solution. The structure is not particularly limited, and commercially available apparatus can be used such as a rotary type thin film evaporator, a plate type falling thin film evaporator, a tube type falling thin film evaporator, a wiper type thin film evaporator, a centrifugation type thin film evaporator and the like. Of these, an evaporator in which thin films are mechanically formed, such as a rotary type, wiper type or centrifugation type thin film evaporator, is preferred. Operation of the thin film evaporator may be carried out under a reduced pressure of generally from 0.1 to 3 KPa, preferably from 0.3 to 2 KPa, at a steam temperature of generally from 70 to 150° C., preferably from 80 to 130° C., and for an average liquid residence time of generally from 30 seconds to 10 minutes, preferably from 1 to 5 minutes. By carrying out the thin film evaporation under these conditions, generally 80% or more, preferably 85% or more, of the solution containing N-vinylformamide is recovered as an evaporated fraction. On the other hand, the remaining unevaporated components, namely the residual high boiling point components, are removed from the system without recycling them into the thin film evaporator.

Alternatively, since the acetone-insoluble components are insoluble not only in acetone but also in methanol and the like, the crude N-vinylformamide containing no acetone-insoluble components may be obtained by adding such a poor solvent thereto to effect precipitation and separation of these components and then evaporating the solvent.

In this connection, since N-vinylformamide is extremely sensitive to thermal changes, the acetone-insoluble components are apt to be generated again even after their removal, so that it is necessary to take special caution not only when the steam fraction containing a crude N-vinylformamide recovered by a thin film evaporator is cooled and condensed, but also when a crude N-vinylformamide is purified by feeding it into a fractionating tower not immediately but after a temporary storage.

When a general organic material is evaporated using a thin film evaporator, the evaporated fraction is recovered in most cases by cooling it to make it once into a condensed solution. In the case of N-vinylformamide, however, it is necessary to take caution because of the aptness to regenerate acetone-insoluble components when the gas-liquid contact time during condensation becomes long. Also, when the condensed solution is fed into a fractionating tower to fractionate a usual organic material, it is preferred in general to carry out preliminary heating prior to its feeding into the fractionating tower, in order to reduce thermal load inside the fractionating tower to a level as small as possible. However, such a method is not preferred in the case of N-vinylformamide, because regeneration of the acetone-insoluble components becomes significant when the heating is too much, and therefore the heating temperature, if necessary, should be limited to generally 50° C. or less, preferably 40° C. or less.

Also, in order to feed a crude N-vinylformamide into a fractionating tower by avoiding generation of the acetone-insoluble components, it is preferred to employ a method in which the crude N-vinylformamide is fed into a thin film evaporator to remove un-evaporated fraction, while simultaneously feeding the evaporated fraction containing N-vinylformamide into the fractionating tower without causing condensation. In that case, it is preferred to feed generally 90% or more, preferably substantially entire portion, of the evaporated fraction in a steam state into the fractionating tower without condensation. In order to effect this purpose, it is necessary to maintain the temperature of the line between the thin film evaporator and the fractionating tower enough high to avoid condensation.

According to the present invention, purification of the N-vinylformamide from which acetone-insoluble components are removed is carried out by continuous distillation using a fractionating tower, and high purity N-vinylformamide having a purity of generally 97% by weight or more, preferably 98% by weight or more, is obtained as the result. The structure of the tower is the same as the case of general fractionating towers, which includes packed bed type, plate column type and the like. The feeding inlet for the crude N-vinylformamide is arranged at a sublevel of the fractionating tower, generally at a ⅕ to ⅘ position from the tower bottom. Though not particularly limited, the distillation may be carried out under industrially feasible operation conditions of generally from 3 to 30, preferably from 5 to 20, as the theoretical plates number of the tower, generally from 0.1 to 3 KPa, preferably from 0.3 to 2 KPa, as the head pressure of the fractionating tower, generally from 50 to 100° C., preferably from 70 to 95° C., as the corresponding tower head temperature, and generally from 80 to 120° C., preferably from 85 to 100° C., as the tower bottom temperature. With regard to the amount of the N-vinylformamide to be distilled from the tower head, it should be set to preferably 90% by weight or less of the N-vinylformamide fraction in the crude N-vinylformamide to be fed into the fractionating tower. In order to obtain the amount exceeding 90% by weight, it is necessary to increase the tower temperature which accelerates decomposition of N-vinylformamide and is therefore not preferable. In this connection, the term "tower head" is used herein in a broad sense including the tower head itself and its surrounding area. In other words, it is possible to employ a method in which trace amounts of low boiling point impurities are removed from the tower head and a fraction containing N-vinylformamide in a large amount is distilled from a surrounding area of the tower head.

In addition, in the purification system of the present invention, a stabilizing agent effective in preventing the thermal polymerization of the N-vinylformamide may be used when the crude N-vinylformamide is fed into the fractionating tower or thin film evaporator. Examples of the effective stabilizing agent include quinones, alkali-modified quinones, phenolic compounds, aromatic amine compounds, thiourea compounds and the like, and these compounds may be added in an amount of generally from 50 to 10,000 ppm, preferably from 100 to 5,000 ppm.

Alkali-modified products of quinones are particularly preferred as the stabilizing agent, and examples of the quinoline compounds include benzoquinones such as p-benzoquinone and o-benzoquinone, naphthoquinones and anthraquinones. Alkali-modified products of these quinones can be prepared by dissolving quinones in a solvent which can easily separate the product by distillation from N-vinylformamide, such as methanol, ethanol, water, toluene, benzene or the like, or directly dissolving in N-vinylformamide, to a concentration of generally from 5 to 150 g/liter, adding an alkali such as sodium hydroxide, potassium hydroxide, sodium carbonate, sodium bicarbonate or the like to the resulting solution and then stirring the mixture at room temperature or with heating. The addition amount of the alkali may be about $10^{-4}$ to $10^{-2}$ mol per liter. Quinones generally act as a polymerization inhibitor, but their alkali-modified products are non-volatile. Therefore, they can be separated easily from N-vinylformamide through the continuous distillation.

The following process is preferred as a specific embodiment for industrially carrying out the present invention. That is, a process for continuously purifying a crude N-vinylformamide, which comprises the steps of:

(1) feeding a crude N-vinylformamide into a thin film evaporator to remove un-evaporated fraction from the system, and feeding a evaporated fraction containing N-vinylformamide into a fractionating tower;

(2) distilling the purified N-vinylformamide from the tower head, and discharging the bottom liquid containing N-vinylformamide from the tower bottom; and (3) recycling the bottom liquid into the thin film evaporator to remove un-evaporated fraction from the system, and feeding the evaporated fraction containing N-vinylformamide into the above described fractionating tower.

According to this process, since the evaporated fraction is again distilled by recycling the bottom liquid into the thin film evaporator for obtaining high purity N-vinylformamide by purifying the crude N-vinylformamide, acetone-insoluble components are hardly accumulated inside the fractionating tower and the yield of purified N-vinylformamide can be increased considerably, so that this process is markedly effective in purifying N-vinylformamide in an industrial scale. It is relatively easy to keep the amount of the acetone-insoluble components in the crude N-vinylformamide at a level of 400 ppm or less by using a thin film evaporator in this process.

Operation conditions of the thin film evaporator and fractionating tower of this process are as described above, but the tower bottom can be kept at a temperature lower than the case of general continuous distillation of N-vinylformamide, by a factor of about 5 to 10° C., usually at 100° C. or less, so that stable distillation operation can be made. Generally 40 to 90%, preferably 50 to 80%, of the N-vinylcarboxylic acid amide component in the crude N-vinylformamide fed into the fractionating tower is distilled from the tower head. When distillation ratio of N-vinylformamide in the fractionating tower is too low, the volume of the fractionating tower bottom liquid becomes so large when the distillate is again fed into the fractionating tower via the thin film evaporator that it is necessary to increase capacities of the thin film evaporator and fractionating tower by enlarging their sizes, which are not advantageous from the industrial point of view. On the other hand, when the distillation ratio of N-vinylformamide in the fractionating tower is too high, the volume of the fractionating tower bottom liquid becomes so small that its residence time at the tower bottom becomes long and accumulation of high boiling point basic impurities on the tower bottom becomes significant, so that the effects of the present invention cannot be exerted sufficiently. In this connection, the basic impurities are a mixture of ammonia, picoline, ethylpicoline and other various basic substances having unknown structures.

Though the purity of the N-vinylformamide of the distillate can be optionally adjusted depending on the intended purity, high purity N-vinylformamide having a purity of generally 97% by weight or more, preferably 98% by weight or more, can be obtained stably. With regard to the composition of the fractionating tower bottom liquid, the N-vinylformamide content becomes generally 50% by weight or more, preferably 60% by weight or more, of the bottom liquid, because the distillation ratio of N-vinylformamide from the tower head is controlled generally at 90% or less according to the present invention.

Next, according to the present invention, the bottom liquid containing N-vinylformamide is discharged continuously from the tower. The thus discharged liquid is fed into a thin film evaporator where un-evaporated fraction is removed from the system, and the evaporated fraction containing N-vinylformamide is recovered and again fed into the above described fractionating tower through its feeding inlet. The ratio of the bottom liquid, which is discharged from the tower and fed into the thin film evaporator, in the bottom liquid is preferably as high as possible, which is generally 50% or more, preferably 80% or more, more preferably 90% or more.

The thin film evaporator into which the discharged bottom liquid is fed is not particularly limited, and the same type and operation conditions of the above described thin film evaporator used in obtaining a crude N-vinylformamide by removing high boiling point components from the thermal decomposition reaction solution can be employed. Also, the discharged liquid from the tower bottom can be recycled into the above described thin film evaporator, and such a method is particularly preferred, because a single thin film evaporator can be used efficiently. In the thin film evaporator, un-evaporated fraction is removed from the system and the evaporated fraction containing N-vinylformamide is recovered, and the evaporated fraction is recycled, as it is or after condensed into liquid, into the above described fractionating tower through its feeding inlet. The above described process of the present invention is constructed by continuously operating each of the distillation by the fractionating tower and the evaporation separation by the thin film evaporator and combining both of the operations.

In the thin film evaporator, un-evaporated fraction is removed from the system and the evaporated fraction is recycled into the above described fractionating tower through its feeding inlet, so that high purity N-vinylformamide can be distilled and recovered with a high yield even when the yield of N-vinylformamide in precision distillation by the fractionating tower is not so high. Since the residence time of the bottom liquid in a fractionating tower is in inverse proportion to evaporation ratio of the distillate in nature, it is necessary to control evaporation ratio of N-vinylformamide at an extremely low level in a method in which N-vinylformamide is simply distilled, in order to prevent decomposition of N-vinylformamide at the bottom of the fractionating tower. According to the present invention, however, decomposition of N-vinylformamide in the bottom of the fractionating tower becomes less, so that high purity N-vinylformamide can be recovered with a high yield.

The above described specification of U.S. Pat. No. 4,814,505 discloses that, in distilling a crude N-vinylformamide with a fractionating tower in the presence of a large amount of formamide, the bottom liquid is circulated with a pump via a thin film evaporator. This is a method commonly used in general distillation to heat the bottom liquid effectively, in which the discharged bottom liquid containing formamide as a main component is heated with a thin film evaporator and the un-evaporated fraction is recycled as such into the tower bottom, but the other fraction evaporated by heat is also recycled into the tower bottom. That is, this method uses the thin film evaporator as a reboiler. In consequence, this conventional method is different from the method of the present invention in which a bottom liquid containing N-vinylformamide as a main component is discharged from the tower bottom and fed into a thin film evaporator, and only the evaporated fraction is recovered and fed into the fractionating tower together with a crude N-vinylformamide.

EXAMPLES

The present invention will be described in more detail with reference to the following Examples, but the invention should not be construed as being limited thereto. In the following examples, all "%" and "ppm" are by weight unless otherwise indicated.

In the examples, acetone-insoluble components in N-vinylformamide were analyzed by the following method.
(Analysis of Acetone-insoluble Component)

At room temperature (25° C.), a 50 g portion of each N-vinylformamide sample was mixed with 250 g of acetone, and the resulting precipitate was collected by filtration using a $0.5\mu$ Teflon filter. This was dried at 60° C. under reduced pressure until a constant weight was reached, and the weight was measured to calculate the content of the high molecular weight components (unit, ppm) according to the formula of (dry weight of insoluble substances/50)$\times 10^6$.

EXAMPLE 1

The great part of methanol was distilled away under reduced pressure from a thermal decomposition reaction solution of N-($\alpha$-methoxyethyl)formamide, thereby obtaining a crude N-vinylformamide (N-vinylformamide, 92%; formamide, 4%; and other organic substances, 4%). The thus obtained crude N-vinylformamide contained 1,000 ppm of acetone-insoluble components. This was evaporated using a thin film evaporator at a steam temperature of 70° C. and under a reduced pressure of 0.4 KPa. The resulting vapor was fed into a fractionating tower as such without causing condensation of the vapor, through a feeding tube whose outside surface was heated and kept at 100° C. using a heater, and 50 hours of continuous distillation was carried out under the following conditions. After completion of the distillation, formation of insoluble polymers was not found at all in the tower. (Distillation Condition in Fractionating Tower)

An apparatus prepared by packing a regular packing material (Sumitomo Through The Labopacking) in a tower of 1 m in length and 5 cm in diameter was used as the fractionating tower for distillation (fractionation) use. A crude N-vinylformamide containing 1,000 ppm of alkali-modified parabenzoquinone as a heat stabilizing agent was continuously fed into a sublevel of the tower to carry out distillation. During the distillation, a crude N-vinylformamide containing 0.5% of the alkali-modified parabenzoquinone as a heat stabilizing agent was continuously fed through the tower head at a ratio of 1,000 ppm to the crude N-vinylformamide to be fed through the sublevel of the tower, and 50% of the N-vinylformamide fed into the fractionating tower was distilled away from the tower head. Under these conditions, N-vinylformamide having a purity of 99.5% was continuously recovered from the tower head.

EXAMPLE 2

Using a thin film evaporator, the crude N-vinylformamide of Example 1 containing 1,000 ppm of acetone-insoluble components was evaporated at a steam temperature of 70° C. and under a reduced pressure of 0.4 KPa, and the resulting vapor was condensed to obtain a crude N-vinylformamide containing 50 ppm of acetone-insoluble components. Using this as the material, 50 hours of continuous distillation was carried out using the fractionating tower under the same conditions as in Example 1. After completion of the distillation, formation of insoluble polymers was not found at all in the tower.

EXAMPLE 3

The crude N-vinylformamide of Example 1 containing 1,000 ppm of acetone-insoluble components was mixed with 5 times weight of acetone, and the thus precipitated acetone-insoluble components were removed by filtration using a $0.5\mu$ Teflon filter. Thereafter, acetone was evaporated under reduced pressure at room temperature to obtain a crude N-vinylformamide containing no acetone-insoluble components. Using this as the material, 50 hours of continuous distillation was carried out using the fractionating tower under the same conditions as in Example 1. After completion of the distillation, formation of insoluble polymers was not found at all in the tower.

COMPARATIVE EXAMPLE 1

Using the fractionating tower,, the crude N-vinylformamide of Example 1 containing 1,000 ppm of acetone-insoluble components was subjected to continuous distillation under the same conditions as in Example 1. After 20 hours of the commencement of distillation, formation of insoluble polymers was already observed.

COMPARATIVE EXAMPLE 2

Using a thin film evaporator, the crude N-vinylformamide of Example 1 containing 1,000 ppm of acetone-insoluble components was evaporated at a steam temperature of 70° C. and under a reduced pressure of 0.4 KPa, and the resulting vapor was condensed to obtain a crude N-vinylformamide containing 50 ppm of acetone-insoluble components. The thus condensed solution was fed into the fractionating tower through a feeding pipe whose outer side was heated at 100° C. The liquid at the inlet of the fractionating tower contained 760 ppm of acetone-insoluble components. Thereafter, 50 hours of continuous distillation was carried out under the same conditions as in Example 1. After 40 hours of the commencement of distillation, formation of insoluble polymers was observed.

EXAMPLE 4

(Production of N-($\alpha$-methoxyethyl)formamide (to be referred to as "ether form" hereinafter)), A 500 liter capacity stainless reactor equipped with a stirrer and a temperature controller was charged with 30 kg of crystal N-($\alpha$-hydroxyethyl)formamide (to be referred to as "hydroxy form" hereinafter) (73% by weight in purity, 0.5% by weight in formamide content and 0.5% by weight in potassium bicarbonate content) which has been obtained by allowing formamide to react with acetaldehyde in the presence of potassium bicarbonate catalyst. To this were added 31.5 kg of methanol (4 mol per mol of hydroxy form) and 0.25 kg of sulfuric acid (corresponds to the total amount of potassium bicarbonate neutralizing amount and 0.5 mol % amount to hydroxy form). With stirring, etherification reaction was carried out at a temperature of 25 to 40° C. for 3 hours until remaining amount of the hydroxy form in the reaction system reached 8% by weight, and the solution was then adjusted to have a pH of 7 by neutralizing the catalyst with 20% by weight of sodium hydroxide. Thereafter, low boiling point components in the solution were evaporated under a reduced pressure of 6.7 KPa, and then the ether form was recovered by distillation under a reduced pressure of 0.4 KPa. (Production of N-vinylformamide)

The ether form obtained above was fed into a stainless steel tube of 40 mm in diameter and 1000 mm in length equipped with a heater, at a rate of 0.2 kg/min under a reduced pressure of 13.3 KPa while keeping temperature in the tube at 400° C., and the exhausted gas was immediately condensed to effect thermal decomposition, thereby recovering 23 kg of distillate (N-vinlyformamide, 67% by weight; methanol, 31% by weight).

(Distillation of Crude N-vinylformamide)

The thus recovered distillate was further distilled at a temperature of 50° C. and under a pressure of 6.7 KPa to remove low boiling point components such as methanol and the like, thereby obtaining a crude N-vinylformamide for distillation treatment use (N-vinylformamide, 88% by weight; formamide, 5% by weight; ether form, 5% by weight; high boiling point impurities, 2% by weight). This crude vinylformamide contained 1,500 ppm of acetone-insoluble compounds.

Separately, p-benzoquinone (parabenzoquinone) was dissolved in methanol to a final concentration by 5% by weight, and sodium hydroxide was added thereto to give a 20 meq/kg. The resulting solution was stirred at 20° C. for 3 hours. When the thus prepared solution was analyzed by a liquid chromatography, p-benzoquinone was not detected (detection limit, 50 ppm) but entirely converted into an alkali-modified product.

As a distillation stabilizing agent, the thus obtained alkali-modified p-benzoquinone (corresponds to 3,000 ppm as p-benzoquinone) was added to the above described crude N-vinylformamide.

Using a thin film evaporator made of glass (50 mm in heat transfer surface diameter and 200 mm in height), the thus prepared crude N-vinylformamide sample was subjected to a distillation treatment under a pressure of 0.4 KPa, at a steam temperature of 125° C. and for an average liquid residence time of 5 minutes.

The un-evaporated fraction was removed from the system without recycling into the thin film evaporator. The condensate of the evaporated fraction (acetone-insoluble components, 50 ppm) was fed as such without heating into a fractionating tower (50 mm in diameter, 900 mm in height, packed with Through The Labopacking.) to carry out precision distillation under a pressure of 6.7 KPa, at a tower head temperature of 70° C., at a tower bottom temperature of 90° C., with a theoretical plate number of 15, at a reflux ratio of a and for a tower bottom residence time of 2.5 hours.

In this case, the above described p-benzoquinone alkali-modified product was continuously added to the condensate so as to give a concentration of 2,000 ppm in terms of p-benzoquinone. The recovery ratio of N-vinylformamide from the tower head in the precision distillation was 70%, and purified N-vinylformamide having a purity of 99% by weight was obtained from the tower head. Also, the bottom liquid was combined with the above described crude N-vinylformamide and fed into the above described thin film evaporator made of glass.

In the recovery operation of N-vinylformamide, substantially no decomposition of N-vinylformamide was observed, accumulation of decomposed products and basic impurities was not found at the tower bottom and high purity (99% by weight) N-vinylformamide was recovered with an integrated yield of 93% (the base of integrated yield is the crude N-vinylformamide).

Figure 1:
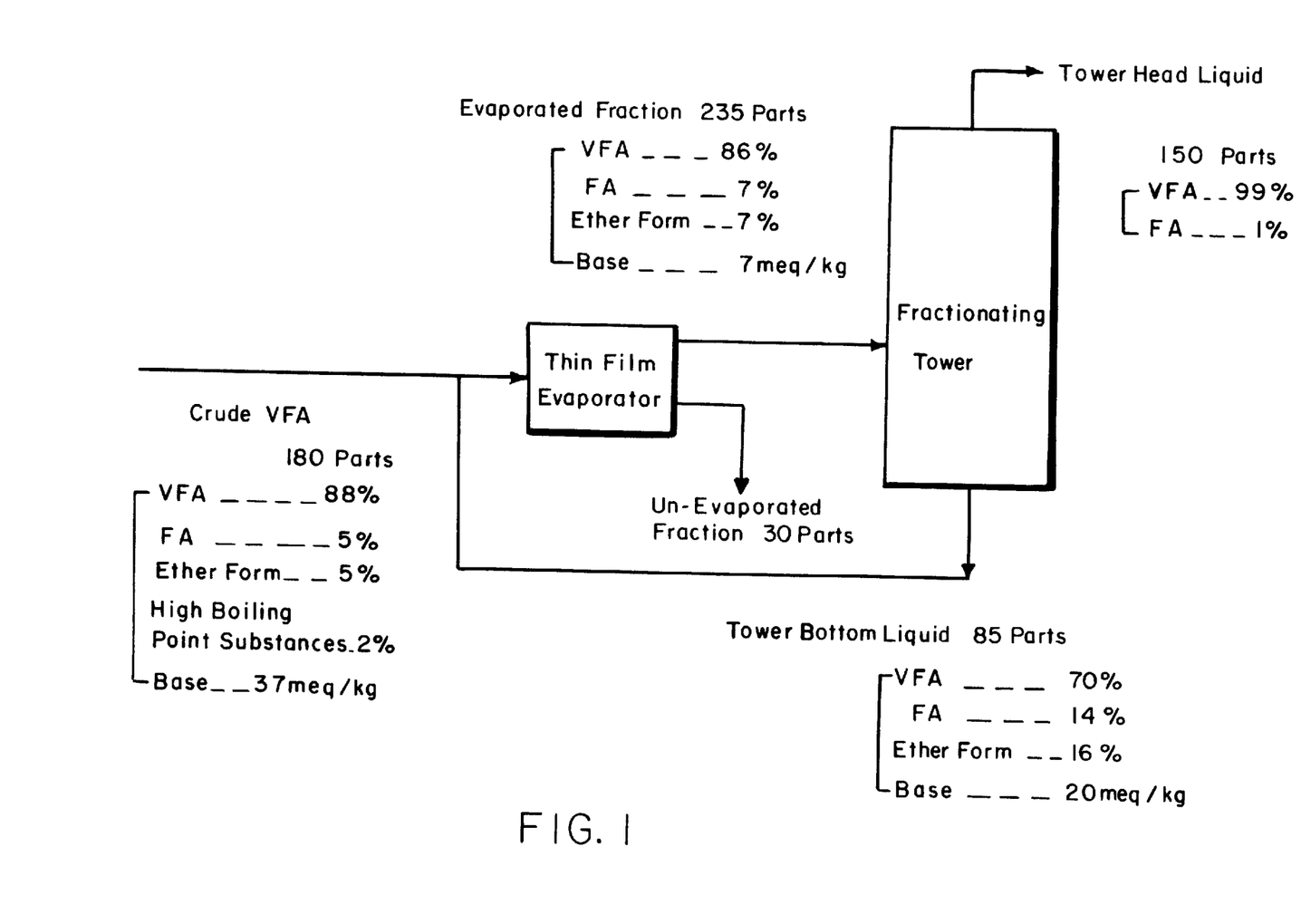
FIG. 1 is a flow sheet showing the N-vinylformamide purification process of inventive Example 4.

A flow sheet showing a relationship under stationary state of the above purification process is shown in FIG. 1. In FIG. 1, "VFA" represents N-vinylformamide, "FA" represents formamide, "ether form" represents N-(a-methoxyethyl) formamide and "base" represents basic impurities. Each component was analyzed by a liquid chromatography. Total amount of basic impurities was obtained by the neutralization titration with 0.1N aqueous solution of sulfuric acid.

COMPARATIVE EXAMPLE 3

In order to obtain N-vinylformamide having a purity of 99% by weight with an integrated yield of about 90% from the same crude N-vinylformamide of Example 4, the process of Example 4 was repeated using the same thin film evaporator made of glass and fractionating tower of Example 4, except that the bottom liquid of the fractionating tower was removed from the system without recycling it into the thin film evaporator. For this purpose, distillation ratio of N-vinylformamide was increased to about 93%, but the tower bottom residence time in the fractionating tower by precise distillation exceeded 10 hours, accumulation of decomposed products and basic impurities at the tower bottom was considerable and temperature increment did not stop when the tower bottom temperature was increased from 90° C. to 110° C., so that the continuous operation failed. The decomposition ratio of N-vinylformamide at the initial stage of distillation was 5%.

Figure 2:
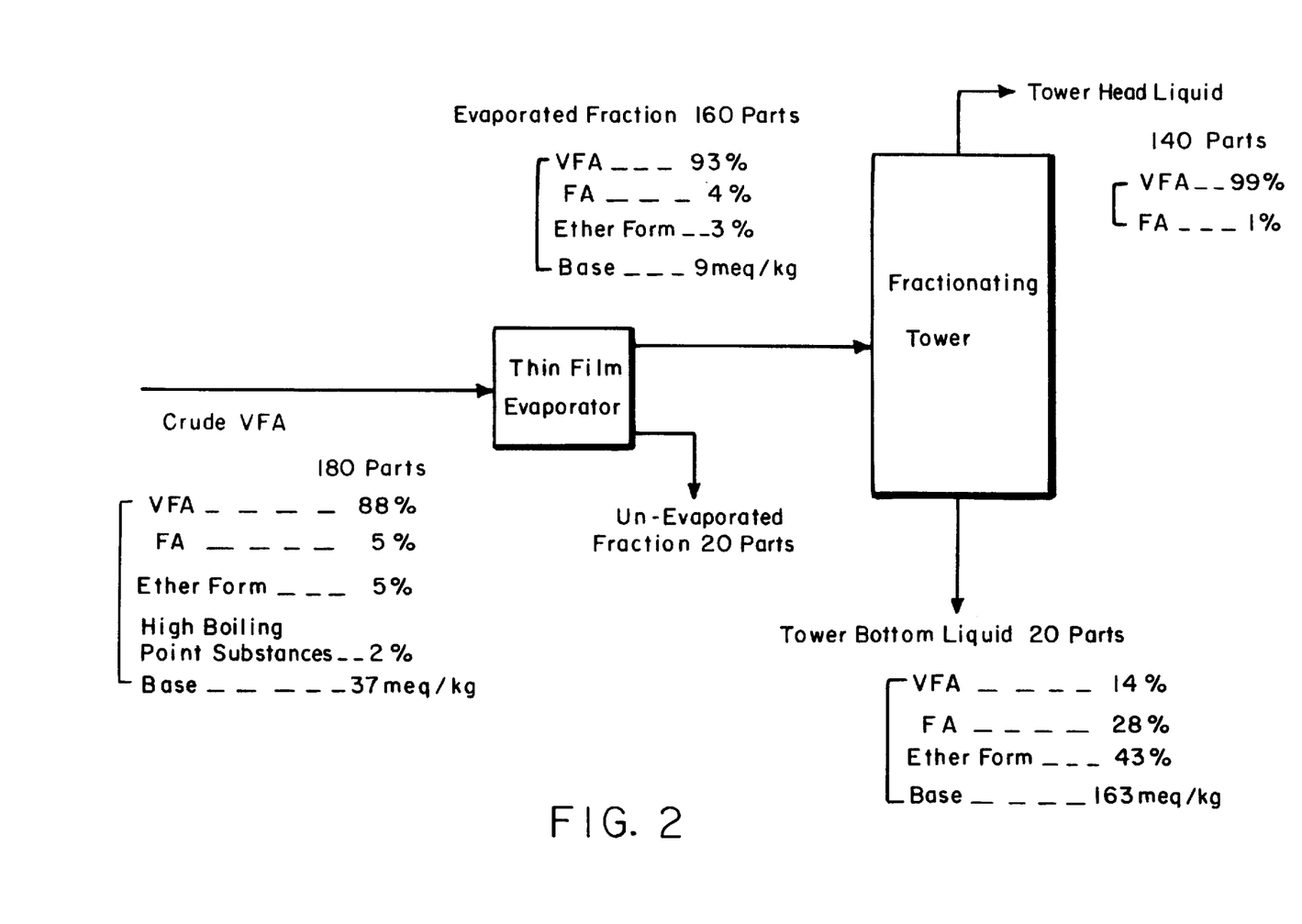
FIG. 2 is a flow sheet showing the N-vinylformamide purification process of comparative Example 3.

A relationship under stationary state of the above purification process is shown in FIG. 2.

Thus, it is apparent that there has been provided, in accordance with the present invention, a process for the purification of a crude N-vinylformamide by distillation, particularly by continuous distillation using a fractionating tower, by which high purity N-vinylformamide can be stably obtained with a high yield while preventing polymerization in the tower.

Particularly, according to the method of claim 11 and the subsequent claims of the present application, in addition to the above effects, high purity N-vinylformamide can be obtained continuously for a prolonged period of time with a high yield without causing accumulation of impurities at the bottom of the fractionating tower, so that this is markedly useful as an industrial scale purification method of N-vinylformamide.

While the invention has been described in detail and with reference to specific examples thereof, it will be apparent to one skilled in the art that various changes and modifications can be made therein without departing from the spirit and scope thereof.

What is claimed is:

1. A purification process of N-vinylformamide, which comprises:

providing a crude N-vinylformamide having an acetone-insoluble component content of not more than 400 ppm; and continuously feeding the crude N-vinylformamide into a fractionating tower, to obtain an N-vinylformamide having high purity.

2. The process according to claim 1, wherein the providing step comprising feeding a crude N-vinylformamide into a thin film evaporator to remove un-evaporated fraction.

3. The process according to claim 2, wherein the providing step further comprising feeding the evaporated fraction containing N-vinylformamide into the fractionating tower in a steam state without causing condensation.

4. The process according to claim 1, wherein the providing step comprising removing acetone-insoluble components from the crude N-vinylformamide by a precipitation separation method using a poor solvent.

5. The process according to claim 1, further comprising distilling N-vinylformamide from the tower head of the fractionating tower in an amount of not more than 90% by weight of the amount of the N-vinylformamide fraction in the crude N-vinylformamide fed into the fractionating tower.

6. The process according to claim 1, wherein the crude N-vinylformamide has an acetone-insoluble component content of not more than 200 ppm.

7. The process according to claim 1, wherein the distillation is carried out under a fractionating tower head pressure of 0.1 to 3 KPa.

8. The process according to claim 1, wherein the crude N-vinylformamide has a formamide content of 1 to 10% by weight.

9. The process according to claim 1, wherein the crude N-vinylformamide has a purity of not less than 80% by weight.

10. The process according to claim 1, wherein the purified N-vinylformamide has a purity of not less than 97% by weight.

11. A continuous purification process of N-vinylformamide, which comprises the steps of:

providing a crude N-vinylformamide;

feeding the crude N-vinylformamide into a thin film evaporator to remove un-evaporated fraction from the system, and feeding the evaporated fraction containing N-vinylformamide into a fractionating tower, distilling the purified N-vinylformamide from the tower head, and discharging a bottom liquid containing N-vinylformamide from the tower bottom, and recycling the bottom liquid into the thin film evaporator to remove un-evaporated fraction from the system, and feeding the evaporated fraction into the fractionating tower.

12. The process according to claim 11, wherein the amount of the purified N-vinylformamide distilled from the tower head is from 40 to 90% by weight of the amount of the N-vinylformamide fraction in the evaporated fraction fed into the fractionating tower.

13. The process according to claim 11, wherein the bottom liquid has an N-vinylformamide content of not less than 50% by weight.

14. The process according to claim 11, wherein the bottom temperature of the fractionating tower is kept at not more than 100° C.

15. The process according to claim 11, wherein the distillation is carried out under a fractionating tower head pressure of 0.1 to 3 KPa.

16. The process according to claim 11, wherein the crude N-vinylformamide has a formamide content of not less than 1 to 10% by weight.

17. The process according to claim 11, wherein the purified N-vinylformamide has a purity of not less than 97% by weight.

18. The process according to claim 11, wherein the evaporated fraction is controlled to have an acetone-insoluble component content of not more than 400 ppm.

19. The process according to claim 11, wherein the feeding of the evaporated fraction is carried out in a steam state without causing condensation.

* * * * *

UNITED STATES PATENT AND TRADEMARK OFFICE
CERTIFICATE OF CORRECTION

PATENT NO. : 5,959,148
DATED : September 28, 1999
INVENTOR(S) : Shin-ichi Sato, et al.

It is certified that error appears in the above-identified patent and that said Letters Patent is hereby corrected as shown below:

On the title page, item [30] Foreign Application Data should read--

April 1, 1996     [JP] Japan..........................8-78672

October 16, 1996 [JP] Japan..........................8-273570

Signed and Sealed this

Thirteenth Day of February, 2001

*Attest:*

NICHOLAS P. GODICI

*Attesting Officer*     Acting Director of the United States Patent and Trademark Office